United States Patent [19]

Yabusaki

[11] 4,388,412

[45] Jun. 14, 1983

[54] IMMUNOASSAY OF PHOSPHOLIPID, SUCH AS PHOSPHATIDYLCHOLINE, IN FLUIDS SUCH AS AMNIOTIC

[75] Inventor: Kenichi K. Yabusaki, Albany, Calif.

[73] Assignee: Hana Biologics, Inc., Emeryville, Calif.

[21] Appl. No.: 344,930

[22] Filed: Feb. 2, 1982

[51] Int. Cl.³ ..................... G01N 33/54; G01N 33/92
[52] U.S. Cl. ..................................... 436/536; 436/63; 436/71; 436/543; 436/547; 436/811; 436/815
[58] Field of Search ............... 436/536, 547, 811, 815, 436/543, 63, 71

[56] References Cited

U.S. PATENT DOCUMENTS

| | | | |
|---|---|---|---|
| 4,233,032 | 11/1980 | Statland | 436/63 |
| 4,257,771 | 3/1981 | Yee | 436/71 |
| 4,290,772 | 9/1981 | Frey | 436/17 |
| 4,292,041 | 9/1981 | Fullerton | 436/71 |

OTHER PUBLICATIONS

D. E. Freer et al., Clin. Chem., 27(10), 1629–1641, (1981).
Chemical Abstracts, 92:142867m (1980).
Chemical Abstracts, 93:128400t (1980).
Chemical Abstracts, 93:112185r and 112186s (1980).

*Primary Examiner*—Sidney Marantz
*Attorney, Agent, or Firm*—Limbach, Limbach & Sutton

[57] ABSTRACT

An immunologic assay for determining the presence of one or more phospholipids in a biological fluid. The method includes adding an ethanolic solution of diacylphosphatidylcholine or alkyltrimethylammonium halide and cholesterol to the biological fluid forming a macromolecular aggregate complex solution. To this solution is added antibody molecules to the phospholipids in an aqueous buffered medium causing an agglutination reaction. The product of the reaction is then examined to determine the presence of the phospholipids.

The method is particularly useful in determining the presence of phosphatidylglycerol in a sample of amniotic fluid. Thus, the assay may be used in evaluating fetal lung maturity.

20 Claims, No Drawings

IMMUNOASSAY OF PHOSPHOLIPID, SUCH AS PHOSPHATIDYLCHOLINE, IN FLUIDS SUCH AS AMNIOTIC

BACKGROUND OF THE INVENTION

It has been found quite useful to know the levels of phospholipids in biological fluids, generally. For example, phospholipids, particularly lecithin, are found in various biological membranes. Further, the phospholipid phosphatidylglycerol, as more fully described below, is found in amniotic fluid and can be used as an indicator of the lung maturity of the fetus. Other phospholipids besides lecithin (phosphatidylcholine) and phosphatidylglycerol which can be detected employing the method disclosed herein are, for example, phosphatidylinositol, phosphatidylserine and phosphatidylethanolamine. Although the present invention will be described in terms of its most preferred embodiment, that is, the determination of phosphatidylglycerol levels in amniotic fluid, the present invention can be used to determine the levels of any of the above-recited phospholipids in biological fluids, generally.

Proper functioning of the pulmonary system is essential for the fetus to survive in an extrauterine environment. Infants born with respiratory difficulties are said to have respiratory distress syndrome (RDS). The primary etiological defect in respiratory distress syndrome is a deficiency of surfactant, a complex mixture of lipids, proteins, and carbohydrates essential to the proper functioning of the mature lung. In the mature lung, phospholipids comprise 90–95% of the lipids. The major surface active phospholipid found in the surfactant is dipalmitoyllecithin. The second major surface active phospholipid is phosphatidylglycerol.

The most direct means of prenatally assessing fetal pulmonary maturity is measuring the production of lung surfactant phospholipids such as phosphatidylcholine (lecithin) and phosphatidylglycerol.

It has been determined that as pregnancy progresses, the sphingomyelin level in the surfactant remains relatively constant, while the lecithin level continues to increase, showing a very sharp increase after the 35th week of gestation. In the mature lung, lecithin comprises at least 50% of the total surfactant lipids. The constant level of sphingomyelin provides an internal reference for comparison with the surface active lecithin, thus providing the basis for the lecithin to sphingomyelin ratio (L/S) test developed by Gluck et al. as described in Am. J. Obstet. Gynecol., 109:440 (1971).

Recent studies by Hallman et al. reported in Am. J. Gynecol., 125:613 (1977), Tsai et al., Clin. Chem., 25:682 (1979), Gotelli et al., Clin. Chem., 24:1144 (1978), and Cunningham et al., Am. J. Obstet. Gynecol., 131:719 (1978), indicate that measurement of phosphatidylglycerol may be of value in determining fetal pulmonary maturity. As alluded to previously, phosphatidylglycerol appears during the 35th–38th gestational week and has a good linear correlation with the L/S ratio. More to the point, Gluck, as reported in Clin. Chem., 23:1107 (1977), points out that only after the appearance of phosphatidylglycerol in amniotic fluid is delivery safe in diabetic mothers. It was also discovered that the presence of blood or meconium in amniotic fluid affects the lecithin to sphingomyelin (L/S) ratio but not the level of phosphatidylglycerol. Although the L/S ratio test has gained wide acceptance as the most reliable prognostic index of fetal pulmonary maturity in most pregnancies, the results must be interpreted with caution for certain maternal complications such as diabetes mellitus, hypertension, severe anemia and intrinsic renal disease, can adversely affect the L/S ratio readings.

It was therefore found desirable to find alternative methods of assessing fetal pulmonary maturity, which are relatively fast, specific and require a minimum amount of skill, experience and sophisticated instrumentation to gain results with high precision and accuracy. It was the development of these alternative methods which led to the present invention for the determination of the presence of phospholipids in a biological fluid. The prior art has used biochemical quantitation and biophysical measurements as techniques for evaluating amniotic fluid surfactant. All of the prior art methods, however, suffer from either being overly time consuming and tedious, and requiring skill and expertise to obtain reasonably high precision, and requiring the use of hazardous chemicals and highly sophisticated and expensive instrumentation or in providing methods which are simply non-specific. The present invention provides a method exhibiting none of these drawbacks.

SUMMARY OF THE INVENTION

The present invention embraces an immunologic assay method for determining the presence of a phospholipid in a biological fluid. By the addition of a defined mixture of a diacylphosphatidylcholine such as, for example, hens egg yolk lecithins or an alkyltrimethylammonium halide such as, for example, hexadecyltrimethylammonium bromide, and cholesterol to the biological fluid, phospholipids present in the biological fluid are incorporated into macromolecular aggregate complexes of lecithin, or alkyltrimethylammonium halide, cholesterol and other biological fluid components. By employing receptor molecules specific for the phospholipids being measured, a sensitive and rapid technique is provided for assessing for the level of specific phospholipids. By combining both the phospholipid, the diacylphosphatidylcholine or alkyltrimethylammonium halide and cholesterol and biological fluid components in the form of the macromolecular aggregate complexes with specific receptors for the phospholipids in a buffered aqueous medium, an agglutination reaction results. The technique is particularly advantageous in determining the presence of phosphatidylglycerol in amniotic fluid.

DETAILED DESCRIPTION OF THE INVENTION

In carrying out the subject method, a known amount of ethanolic solution of cholesterol and a diacylphosphatidylcholine such as hens egg yolk lecithins or a known amount of ethanolic solution of cholesterol and an alkyltrimethylammonium halide such as hexadecyltrimethylammonium bromide are added to a known volume of biological fluid. When amniotic fluid is used as a biological fluid, it is first centrifuged and the ethanolic solution added to the centrifugate. After mixing, an additional known volume of centrifuged amniotic fluid is added and if phosphatidylglycerol is present in the amniotic fluid sample, macromolecular aggregates are formed of the diacylphosphatidylcholine or alkyltrimethylammonium halide, cholesterol, phosphatidylglycerol and other amniotic fluid components. The addition of a known volume of the phosphatidylglycerol macromolecular aggregate complex solution to a known amount of antibody molecules to phosphatidylglycerol in a buffered aqueous medium results in an agglutination reaction indicating the presence of phosphatidylglycerol.

The above-described method can be carried out using relatively small quantities of biological fluid. For example, the phosphatidylglycerol level can be determined in amniotic fluid obtained by transabdominal amniocentesis producing less than 3.0 ml amniotic fluid. In fact, the above-described method can be carried out employing usually no more than 1 ml of the biological fluid.

The ethanolic solution of cholesterol and diacylphosphatidylcholine will contain cholesterol in the range of approximately 0.5 to 12 mg/ml, more usually 5 to 10 mg/ml and most preferably 8 to 9 mg/ml and hens egg yolk lecithins in the range of 0.05 to 10 mg/ml, more usually 0.5 to 3 mg/ml and most preferably approximately 1.5 to 2.0 mg/ml.

The ethanolic solution of cholesterol and alkyltrimethylammonium halide will contain cholesterol in the range of approximately 0.5 to 12 mg/ml, more usually 5 to 10 mg/ml and most preferably 8 to 9 mg/ml and hexadecyltrimethylammonium bromide in the range of 0.1 to 5 mg/ml, more usually 0.5 to 3 mg/ml, and most preferably approximately 1 to 2 mg/ml.

The antibodies to phosphatidylglycerol will be buffered in the range of approximately pH 5 to 10, more usually approximately 5.5 to 8.0 and most preferably approximately 6.5 to 7.0. Various buffers may be used such as Tris, phosphate and the like, while the preferred buffer is the phosphate. The concentration of buffer will generally be in the range of approximately 0.001 to 0.5 Molar, more usually in the range of approximately 0.005 to 0.1 Molar and preferably approximately 0.0175 to 0.05 Molar.

Other additives may also be in the assay medium which are employed for preserving or protecting individual components or reagents or for aiding the performance characteristics of the assay. Particularly, sodium chloride can be employed in amounts of approximately 0.01 to 5 weight percent, more usually approximately 0.05 to 2.0 weight percent and preferably approximately 0.5 to 1.0 weight percent.

The quantity of diacylphosphatidylcholines or alkyltrimethylammonium halides and cholesterol which are added to the biological fluid must be added in a quantity large enough to allow the distribution of the phospholipids if present in the biological fluid sample to distribute into macromolecular aggregates such that the antibody molecules to the phospholipids can effectively bind to the phospholipid molecules. The amount of antibody to phospholipid which is employed will vary and be chosen to provide the desired agglutination reaction.

EXAMPLE

A. Preparation of Phosphatidylglycerol Immunogen Complex

Approximately 45 mg L-phosphatidyl-DL-glycerol (0.058 mMole) in chloroform and approximately 270 mg hens egg yolk lecithins (0.34 mMole) in methanol were dried under a stream of nitrogen gas and dissolved in approximately 10 ml of absolute ethanol and placed in a 500 ml Erlenmeyer flask. To the L-phosphatidyl-DL-glycerol-lecithin solution is added 1.35 grams of cholesterol which was dissolved in approximately 135 ml of absolute ethanol.

To the above mixture was added 145 ml of 0.0175 Molar sodium phosphate buffer, pH 6.0. This resulted in the formation of a white colloidal emulsion which was allowed to stir for 15 minutes at room temperature and then centrifuged at approximately 13,000×g for 10 minutes at 4° C. The resulting pellet was resuspended in a 2% methylated bovine serum albumin solution in 0.0175 Molar sodium phosphate buffer, pH 6.0. The resulting L-phosphatidyl-DL-glycerol:Lecithin:cholesterol:m-BSA complex was left overnight at 4° C.

Four milliliter aliquots of the L-phosphatidyl-DL-glycerol-immunogen solution was lyophilized and the resulting powder stored at −20° C.

B. Anti-phosphatidylglycerol Antibodies

The lyophilized phosphatidylglycerol-immunogen complex prepared above was suspended in 4 ml of sterile distilled water by vortexing and thorough mixing such that the final concentration of the immunogenic protein was 20 mg/ml.

Approximately 0.5 ml aliquot of the above phosphatidylglycerol-immunogen complex was injected intravenously per rabbit every two days for a period of three successive weeks. The total dosage was about 4.5 ml at 20 mg immunogenic protein per milliliter. After the last injection, a period of 5 to 7 days was allowed to pass and the rabbit bled by heart puncture. When the desired amount of blood was collected (about 20–30 ml) the blood was allowed to clot and the clot removed. The remaining solution was centrifuged at 2,000 RPM for 10 minutes. The serum was collected free of loose red blood cells resulting in collection of the anti-phosphatidylglycerol anti-serum.

Subsequently, rabbits which were found to be immune were subjected once a month to the following injection protocol. Rabbits were injected intravenously once very two days over a period of one week with 0.5 ml per injection of the phosphatidylglycerol-immunogen described above and bled via heart puncture 5 to 7 days after the last injection. The blood was collected and processed as described above.

C. Purification of Anti-Phosphatidylglycerol Antiserum

To a known volume of rabbit serum containing a high titer of anti-phosphatidylglycerol activity is slowly added half of the above volume of a freshly prepared saturated solution of ammonium sulfate which has been adjusted to a pH of approximately 7.8 with 2 Normal NaOH. This solution was stirred at room temperature for approximately two hours and then centrifuged at 1400×g for 30 minutes at approximately 4° C. The pellet was dissolved in a minimum of 0.85% NaCl and then dialyzed against 0.0175 Molar sodium phosphate buffer, pH 6.5, containing 0.85% NaCl for two days at 4° C. with several changes of the above mentioned buffer. The contents of the dialysis bag were centrifuged at 1400×g for 30 minutes, resulting in an IgG rich supernatant.

The above-derived IgG fraction was then cleansed of interfering anti-cholesterol antibodies by the following procedure. Approximately 0.085 ml of the IgG fraction in approximately 0.0175 Molar sodium phosphate buffer, pH 6.5 containing approximately 0.85% NaCl was mixed with approximately 0.11 ml of an ethanolic solution containing 0.15% hens egg yolk lecithins and 0.9% cholesterol. Then an additional 0.8 ml of the IgG fraction was added and the entire mixture thoroughly mixed then centrifuged at full speed for 4 minutes in a microcentrifuge. The resulting supernatant was termed cholesterol absorbed anti-phosphatidylglycerol fraction. The antibody solution was diluted appropriately to give the desired agglutination reaction with standardized control solutions containing known amounts of phosphatidylglycerol. The dilutant for the anti-phosphatidylglycerol antibodies was 0.0175 Molar sodium phosphate buffer, pH 6.0 containing 1.0% NaCl.

D. Preparation of the Lecithin-Cholesterol Reagent

Possibly 90 mg of cholesterol was dissolved in approximately 9.5 ml of absolute ethanol by heating the solution under a stream of hot tap water. After cooling, the final volume was made to 10.0 ml with the addition of 15 mg of purified hens egg yolk lecithins in approximately 0.5 ml of absolute ethanol.

E. Preparation of the Hexadecyltrimethylammonium Bromide-Cholesterol Reagent

Possibly 90 mg of cholesterol was dissolved in approximately 9.5 ml of absolute ethanol by heating the solution under a stream of hot tap water. After cooling, the final volume was made to 10.0 ml with the addition of 10 mg of hexadecyltrimethylammonium bromide in approximately 0.5 ml of absolute ethanol.

F. Agglutination Test for Phosphatidylglycerol Reagents (1)

a. Lecithin-cholesterol reagent approximately 0.15% lecithin, approximately 0.9% cholesterol (Reagent A) or
b. Hexadecyltrimethylammonium bromide-cholesterol reagent approximately 0.1% hexadecyltrimethylammonium bromide, approximately 0.9% cholesterol (Reagent A)
2. Anti-phosphatidylglycerol antibody solution (Reagent B)

G. Agglutination Test for Phosphatidylglycerol Reagents

1. Lecithin-cholesterol reagent approximately 0.15% lecithin, approximately 0.9% cholesterol (Reagent A)
2. Anti-phosphatidylglycerol antibody solution (Reagent B)
3. Positive and negative control solutions. Positive control contains approximately 2 micrograms per ml phosphatidylglycerol and 40 micrograms per ml of lecithin. Negative control contains 40 micrograms per ml of lecithin only.

A disposable 12×75 mm test tube was appropriately marked for each sample and control sample to be assayed. To each respective test tube was added approximately 0.085 ml of supernatant from a centrifuged amniotic fluid sample and/or 0.085 ml of the positive and negative control samples. To each test tube was then added dropwise approximately 0.11 ml of Reagent A while constantly shaking the tube and finally vortexing the contents of the test tube to provide for thorough mixing. Then to each test tube was added an additional approximately 0.8 ml of the respective centrifuged amniotic fluid sample and/or control (positive and negative) samples and (the contents of each test tube) mixed thoroughly by vortexing.

Approximately 0.025 ml of the anti-phosphatidylglycerol solution (Reagent B) was pipetted onto the centers of separate test rings of an agglutination slide for each sample and control to be assayed. This was followed by the pipetting of approximately 0.01 ml of each amniotic fluid and positive and negative control sample macromolecular aggregate solutions onto the centers of the anti-phosphatidylglycerol antibody droplets in the centers of the separate test rings of the agglutination slide. Each macromolecular aggregate solution was mixed thoroughly before an aliquot was removed via pipetting. The agglutination slide was then placed on the platform of a serological rotor and rotated at a constant speed of, for example, approximately 180 revolutions per minute for approximately ten minutes. The slide was then placed on a mirror and the droplets in each test ring examined. A positive reaction for the presence of phosphatidylglycerol is indicated by the appearance of large agglutination particles as in the ring containing the positive control sample. A negative reaction shows a slightly grainy appearance but without large agglutinated particles as in the ring containing the negative control sample.

Although the above recited example is particularly directed toward the determination of the presence of phosphatidylglycerol in a sample of amniotic fluid, the technique shown and described is equally valuable in determining the presence of phospholipids, generally, in a biological fluid.

What is claimed is:

1. A method of determining the presence of a phospholipid in a biological fluid comprising:
   A. adding an ethanolic solution of diacylphosphatidylcholine and cholesterol to the biological fluid forming a macromolecular aggregate complex solution;
   B. adding the macromolecular aggregate complex solution to antibody molecules to the phospholipid in an aqueous buffered medium causing an agglutination reaction; and
   C. examining the results of the agglutination reaction to determine the presence of the phospholipid.

2. A method of determining the presence of a phospholipid in a biological fluid comprising:
   A. adding an ethanolic solution of an alkyltrimethylammonium halide and cholesterol to the biological fluid forming a macromolecular aggregate complex solution;
   B. adding the macromolecular aggregate complex solution to antibody molecules to the phospholipid in an aqueous buffered medium causing an agglutination reaction; and
   C. examining the results of the agglutination reaction to determine the presence of the phospholipid.

3. The method of claims 1 or 2 wherein the phospholipid is a member from the group consisting of phosphatidylcholine, phosphatidylinositol, phosphatidylserine, phosphatidylethanolamine and phosphatidylglycerol.

4. The method of claims 1 or 2 wherein the biological fluid comprises amniotic fluid.

5. The method of claim 4 wherein the phospholipid comprises phosphatidylglycerol.

6. The method of claim 1 wherein sufficient diacylphosphatidylcholine and cholesterol are added to the biological fluid such that the phospholipid-containing macromolecular aggregates can be bound to the antibody molecules.

7. The method of claim 2 wherein sufficient alkyltrimethylammonium halide and cholesterol are added to the biological fluid such that the phospholipid containing macromolecular aggregates can be bound to the antibody molecules.

8. A method of determining the presence of phosphatidylglycerol in a sample of amniotic fluid comprising:
   A. adding an ethanolic solution of diacylphosphatidylcholine and cholesterol to a sample of amniotic fluid;
   B. adding an additional quantity of amniotic fluid to the solution of subpart A forming macromolecular aggregates of lecithin, cholesterol and phosphatidylglycerol;
   C. forming an agglutination reaction by adding the phosphatidylglycerol macromolecular aggregate complex containing solution to a known quantity of antibody molecules to the phosphatidylglycerol in a buffered aqueous medium; and
   D. examining the results of the agglutination reaction to determine the presence of the phosphatidylglycerol.

9. A method of determining the presence of phosphatidylglycerol in a sample of amniotic fluid comprising:
   A. adding an ethanolic solution of alkyltrimethylammonium halide and cholesterol to a sample of amniotic fluid;
   B. adding an additional quantity of amniotic fluid to the solution of subpart A forming macromolecular aggregates of alkyltrimethylammonium halide, cholesterol and phosphatidylglycerol;
   C. forming an agglutination reaction by adding the phosphatidylglycerol macromolecular aggregate complex containing solution to a known quantity of antibody molecules to the phosphatidylglycerol in an aqueous buffered medium; and
   D. examining the results of the agglutination reaction to determine the presence of the phosphatidylglycerol.

10. The method of claims 8 or 9 wherein the buffered aqueous medium containing the antibodies to phosphatidylglycerol is buffered in the pH range of approximately 5 to 10.

11. The method of claim 8 or 9 wherein the buffered aqueous medium containing the antibodies to phosphatidylglycerol is buffered in the pH range of approximately 5.5 to 8.0.

12. The method of claims 8 or 9 wherein the buffered aqueous medium containing the antibodies to phosphatidylglycerol is buffered in the pH range of approximately 6.5 to 7.0.

13. The method of claims 8 or 9 wherein the aqueous medium is buffered with a phosphate buffer.

14. The method of claims 1 or 2 wherein the complex solution further comprises sodium chloride.

15. The method of claims 8 or 9 wherein the complex solution further comprises sodium chloride.

16. The method of claim 15 wherein the sodium chloride is present in an amount between approximately 0.01 to 5.0 weight percent.

17. The method of claim 15 wherein the sodium chloride is present in an amount between approximately 0.05 to 2.0 weight percent.

18. The method of claim 15 wherein the sodium chloride is present in an amount between approximately 0.5 to 1.0 weight percent.

19. The method of claims 1 or 8 wherein the diacylphosphatidylcholine comprises hens egg yolk lecithin.

20. The method of claims 2 or 9 wherein the alkyltrimethylammonium halide is hexadecyltrimethylammonium bromide.

* * * * *

UNITED STATES PATENT OFFICE
CERTIFICATE OF CORRECTION

Patent No. 4,388,412          Dated   June 14, 1983

Inventor(s)  Kenichi K. Yabusaki

It is certified that error appears in the above-identified patent and that said Letters Patent are hereby corrected as shown below:

In column 3, line 23, after "and" (second occurrence) insert --alkyltrimethylammonium halide such as--.

In column 5, lines 14 and 23, change "Possibly" to --Approximately-- in each instance.

In column 5, line 33, delete "(1)".

In column 5, line 34, insert --1.-- before "a.".

In column 5, lines 41-47, delete the material beginning "2. Anti-phosphatidylglycerol antibody" and ending with "0.9% cholesterol (Reagent A)".

*Signed and Sealed this*

*Twentieth* Day of *March 1984*

[SEAL]

Attest:

GERALD J. MOSSINGHOFF

*Attesting Officer*      *Commissioner of Patents and Trademarks*